United States Patent [19]

Swaminathan et al.

[11] Patent Number: 5,140,528

[45] Date of Patent: Aug. 18, 1992

[54] METHOD FOR EVALUATING RELATIONSHIP BETWEEN THE SIZE OF DISCONTINUITY INDICATIONS FROM NON-DESTRUCTIVE EXAMINATION OF A TURBINE ROTOR, STRESS APPLIED TO THE ROTOR AND REMAINING LIFE OF THE ROTOR

[75] Inventors: V. P. Swaminathan, San Antonio, Tex.; Richard H. Marloff, Monroeville, Pa.

[73] Assignee: Westinghouse Electric Corp., Pittsburgh, Pa.

[21] Appl. No.: 205,892

[22] Filed: Jun. 13, 1988

[51] Int. Cl.$^5$ ............................................. G01M 7/00
[52] U.S. Cl. ................................... 364/508; 364/506
[58] Field of Search ....................... 364/508, 507, 506; 73/592, 660, 65.9

[56] References Cited

U.S. PATENT DOCUMENTS 4,764,882 8/1988 Braschel et al. .................... 364/508

FOREIGN PATENT DOCUMENTS 0475602 10/1975 Australia .............................. 364/508

OTHER PUBLICATIONS

O'Donoghue et al., "Analysis of Interaction Behavior of Surface Flaws in Pressure Vessels", Georgia Institute of Technology, Atlanta, Georgia.
O'Donoghue et al., "Multiple Surface Cracks in Pressure Vessels". *Engineering Fracture Mechanics*, vol. 20, No. 3, pp. 545–560, 1984.
O'Donoghue et al., "Multiple Coplanar Embedded Elliptical Cracks in an Infinite Solid Subject to Arbitrary Crack Face Tracks", International Journal for Numerical Methods in Engineering, vol. 21, 437–449 (1985).
Dowling, "Fatigue Life Prediction for Complex Load versus Time Histories", *Journal of Engineering Material Technology*, vol. 105, No. 3, pp. 206–214, 1983.
Safer: Report Summaries, Table of Contents for Volumes 1–4, pp. 6-1 to 6-2 of vol. 1 and pp. 3-1 to 3-3 of vol. 3, 1988.
A. Saxena, P. K. Liaw, W. A. Logsdon & V. E. Hulina, "Residual Life Prediction and Retirement for Cause Criteria for SSTG Casings, Part II: Fracture Mechanics Analysis", *Engineering Fracture Mechanics*, vol. 25, p. 289, 1986.
H. C. Argo & B. B. Seth, "Fracture Mechanics Analysis of Ultrasonic Indications in Cr–Mo–V Steel Turbine Rotors", in *Case Studies in Fracture Mechanics*, Ed. J. P. Rich & D. J. Cartwright, 1977.
A. Saxena, R. S. Williams & T. T. Shih, "Influence of Holdtime on Elevated Temperatue Fatigue Crack Growth Behavior", in *Fracture Mechanics: Thirteenth Conference*, ASTM STP 700, 1980, pp. 112–130.
V. P. Swaminathan & J. D. Landes, "Temperature Dependence of Fracture Toughness of Large Steam Turbine Forgings Produced by Advanced Steel Melting Processes," Fracture Mechanics: Fifteenth Symposium, ASTM STP 833, R. J. Sanford Ed., ASTM, 1984.
D. P. Rooke & D. J. Cartwright, "Stress Intensity Factors" 1976.
Westinghouse ONCALL COMPRO Computerized Procedures 1984 four pages 364/492.

*Primary Examiner*—Dale M. Shaw
*Assistant Examiner*—S. A. Melnick
*Attorney, Agent, or Firm*—G. H. Telfer

[57] ABSTRACT

A method of analyzing crack growth in an object takes into account interaction between indications of discontinuities that can become cracks and also effects of creep on crack growth to provide a more accurate analysis of crack growth. The remaining life of an object is determined by calculating a critical crack size from worst case conditions and defining loading blocks representing cycles of temperature and stress changes. The rate of growth in the size of indications estimated from non-destructive evaluation is accumulated based upon the defined loading blocks until one of the indications reaches the critical crack size. The allowable stress which can be placed upon the object can be calculated from the same estimates of indication size and assuming different stress levels until a desired lifetime of the object is attained when one of the indications reaches the critical crack size. An initial allowable discontinuity indication size can be calculated by setting a current crack size to the critical crack size and decrementing the current crack size until the defined loading blocks have been applied to the current crack size in reverse order while calculating the effective crack growth rate including the effects of creep.

16 Claims, 6 Drawing Sheets

METHOD FOR EVALUATING RELATIONSHIP BETWEEN THE SIZE OF DISCONTINUITY INDICATIONS FROM NON-DESTRUCTIVE EXAMINATION OF A TURBINE ROTOR, STRESS APPLIED TO THE ROTOR AND REMAINING LIFE OF THE ROTOR

BACKGROUND OF THE INVENTION

1. Field of the Invention

The present invention is related to the evaluation of discontinuity indications from non-destructive testing of objects to determine a relationship between indication size, stress applied to the object and remaining life of the object and, more particularly, to a method of determining initial allowable indication size, allowable stress and remaining life of a high pressure turbine rotor based upon ultrasonic and magnetic particle testing results.

2. Description of the Related Art

Many types of equipment and components undergo non-destructive testing or evaluation both during the manufacturing process for quality control and during maintenance to help make decisions regarding repair. Tests which are used in performing non-destructive evaluation (NDE) include ultrasonic testing and magnetic particle testing. Ultrasonic testing can be used on virtually any object with the proper selection of frequency and the construction and arrangement of transducers. Ultrasonic testing produces indications of change in composition or structure of an object including detection of minute holes or other discontinuities of structure in the interior of an object. In addition, if an object can be used to form an electromagnet, e.g., if constructed of a ferrous metal, similar discontinuities in structure or composition on the surface of the object which are difficult to detect optically can be revealed using magnetic particle testing. This method uses iron filings which indicate the fluctuations in a magnetic field formed by the object used as an electromagnet.

Both of these types of NDE are customarily used to test objects such as rotors for electricity generating turbines. A variety of methods of analyzing the data resulting from such testing is known for predicting the growth of cracks at the discontinuity indications. Typically, linear-elastic and elastic-plastic fracture mechanics (LEFM and EPFM) are used to evaluate rotors. However, high pressure and intermediate pressure steam turbine rotors are subjected to temperatures at which creep is a factor in the growth of cracks. The effects of creep are time dependent, i.e., the length of time a rotor is exposed to stress at elevated temperatures affects the crack growth rate due to creep. Conventional LEFM and EPFM analysis does not take into account time-dependent factors including creep. As a result, use of LEFM and EPFM alone in analyzing NDE indications for high pressure and intermediate pressure steam turbine rotors can result in significantly underestimating the rate of crack growth.

SUMMARY OF THE INVENTION

An object of the present invention is to provide a method for analyzing NDE discontinuity indications taking into account creep and creep-fatigue crack growth.

Another object of the present invention is to provide an estimate of the remaining life of an object by analyzing NDE discontinuity indications.

A further object of the present invention is to provide a method for calculating an initial allowable indication size from estimates of critical crack size and stress to which an object will be exposed during an expected lifetime.

Yet another object of the present invention is to provide a method for calculating allowable stress for an object based upon characteristics of the material composing the object, the amount of stress expected to be applied to the object and NDE discontinuity indications or estimates of indication size.

The above objects are obtained by providing a method for evaluating effects of stress on an object after analysis to detect indications of discontinuities in the object, comprising the steps of: identifying indications likely to interact, categorizing by interaction type each of the indications identified, and applying different models of crack growth to the indications in dependence upon the interaction type determined by the identifying and the categorizing to determine a relationship between indication size, stress applied to the object and remaining life of the object. Preferably, the models of crack growth include effects of creep when at least part of the stress is applied to the object at a temperature where creep is a significant factor for the material composing the object. Also, the method preferably includes combining interacting indications within a minimum ligament distance to produce a new indication and applying the models of crack growth applicable to the new indication produced by combining the interacting indications.

This method can be used to determine the remaining life of an object by including the steps of defining the stress applied to and temperature of the object, as a function of time, calculating a maximum stress intensity factor for each of the indications, accumulating change in the indication size of the indications over a period of time, combining interacting indications within a minimum ligament distance to produce a new indication and repeating the just described steps of calculating and accumulating until the indication size of one of the indications is at least as large as a critical crack size.

The method can also be used to determine an allowable stress for the object by including the steps of calculating a maximum stress intensity factor for one of the indications, initializing crack size to a size represented by the one of the indications, accumulating crack growth as a function of time at an assumed stress level by applying a model of crack growth selected for the one of the indications until the crack size is at least as large as a critical crack size, comparing an amount of time represented by the crack growth previously accumulated with a desired lifetime for the object and repeating the just described steps of initializing, accumulating, and comparing after changing the assumed stress level if the comparing step finds the amount of time and the desired lifetime of the object to be substantially different and otherwise outputting the assumed stress level as an allowable stress for the object.

Another embodiment of the present invention includes evaluating effects of stress on an object, at least part of the stress being applied at a temperature where creep is a significant factor for the material composing the object, comprising the steps of establishing a relationship between time and stress applied to and temperature of the object, calculating a critical crack size for worst case conditions, assigning an initial value to a current crack size, calculating a maximum stress intensity factor and a crack growth rate for the current crack size in dependence upon the established relationship between time and stress including effects of creep, and changing the current crack size until one of remaining life of the object and an initial allowable discontinuity indication size is determined. Where the stress varies cyclically over time, the method preferably includes accumulating cycles of stress changes defined in loading blocks.

The method can be used to determine an initial allowable indication size by assigning the critical crack size to the current crack size when the current crack size is initialized, decrementing the current crack size when the current crack size is changed and repeating the calculating, accumulating, and changing steps until a number of loading blocks is substantially equivalent to a desired lifetime of the object so that the current crack size can be output as the initial allowable indication size.

Yet another embodiment of the present invention includes evaluating effects of stress on a turbine rotor exposed to cyclical changes in stress and temperature, comprising the steps of obtaining an estimate of at least one indication of discontinuity in material composing the turbine rotor, recording in machine readable form a number of loading blocks defining cycles of temperature and stress upon the turbine rotor, and applying different models of crack growth to the indication of discontinuity, including effects of interactions between indications when estimates for more than one indication are obtained, and including effects of creep when the recorded loading blocks include exposure of the turbine rotor to a temperature where creep is a significant factor in crack growth in the material composing the turbine rotor.

These objects, together with other objects and advantages which will be subsequently apparent, reside in the details of construction and operation as more fully hereinafter described and claimed, reference being had to the accompanying drawings forming a part hereof, wherein like reference numerals refer to like parts throughout.

DESCRIPTION OF THE PREFERRED EMBODIMENTS

There are several improvements which the present invention has made over methods used in the prior art to analyze NDE indications. All of the improvements have been incorporated into the flowchart illustrated in FIGS. 1A-1F. The first step 10 is to select a rotor or other object for analysis. The rotor is selected from among those for which NDE data is available or for which estimates of certain characteristics have been made as described below. Next, a mode of analysis is selected in step 12. In addition to analyzing the interaction of NDE indications, the method according to the present invention includes performing creep-crack initiation analysis and calculation of an initial allowable indication size.

In step 14, it is determined whether or not NDE indications are to be analyzed. If not, a determination is made in step 16 of whether creep-crack initiation analysis has been selected. The analysis of creep-crack initiation at step 18 may use conventional analysis techniques.

If it was determined at step 14 that analysis of NDE indications was selected in step 12, a check is made at step 20 to verify that an NDE file is available for the rotor selected in step 10. As noted above, certain types of analysis can be performed using estimates of certain characteristics. If the NDE file is not available, an initial indication size is input at step 22. If it is determined in step 20 that the NDE data is available for the selected rotor, step 24 reads in NDE data from the NDE file 26.

One of the key features of the present invention is how interactions between indications are handled. In the case of a turbine rotor, NDE data include indications of discontinuity from ultrasonic (sonic) and magnetic particles (MP) testing. The present invention can be applied to the near-bore region of a turbine rotor where the magnetic particle tests are made on the interior surface of the rotor surrounding the central bore and the ultrasonic testing provides discontinuity indications from the region surrounding the bore to a selected radial distance. Thus, once the NDE data is read, in step 24, it is necessary to determine the likelihood of sonic-sonic, sonic-MP and MP-MP interactions. In addition, sonic indications close to the surface of the bore where no MP indications are present may interact with the surface of the bore.

In step 28, interacting indications are identified. In the case of conventional turbine rotors, if the distance between indications or between indications and the bore is greater than three times the size of the indication, the indication may be considered to be isolated and no interaction needs to be considered. If, on the other hand, the distance between indications or between an indication and the bore is less than or equal to three times the size of the indication, interaction between the indications or indication and bore needs to be taken into account.

The value used for size of the indication depends upon the type of test which produces the indication. A conservative value for sonic indications is to assume that each indication represents a sphere with a diameter (D) calculated from an estimated area of the indication. The area of the indication is estimated from a reflected signal as is known in the art. The diameter of the indication is used as the size of the indication in evaluating interactions in step 28. A close group of sonic indications are considered together as a "stringer" indication. The estimated area of the largest indication in a stringer group is used to calculate a diameter corresponding to the size of the stringer indication. All MP indications on the surface of the bore may be conservatively assumed to have a size of 3.2 mm (0.125 inch) corresponding to the depth of a crack represented by the indication.

After all interacting indications have been identified in step 28 by determining which indications have a ligament distance (S) to indication size (D) ratio that is less than or equal to three, the indications are categorized based upon geometry. The NDE data provides both size and location information for each of the indications. Part of the identifying process of step 28 includes combining indications. A conservative assumption may be made that any two indications being evaluated represent co-planar cracks. All combining is preferably conducted two indications at a time. Any two indications having a ligament distance to indication size ratio (S/D) less than or equal to 0.1 are merged to form a new indication having a size equal to the sum of the size of each indication plus the ligament distance. Step 28 includes combining all such indications into new indications until the S/D ratio between every possible combination of two indications is greater than 0.1.

After all initial combining of indications has been completed, the remaining indications, both original and combined indications, are categorized in step 30. All indications which have S/D ratios greater than three for all neighboring indications are classified as isolated or non-interacting. The interacting pairs are classified as sonic interactions, sonic-MP interactions, sonic-surface interactions, or MP-MP interactions.

After the NDE indications have been evaluated and categorized in steps 28 and 30 or an initial size has been input in step 22, one of two types of analysis is selected in step 32. It is possible to calculate the remaining life of the rotor (or another object) or to calculate allowable stress for a desired lifetime of the object. If it is determined in step 34 that an allowable stress calculation was selected, a determination is made in step 36 as to whether conventional methodology in step 38 should be used or the interacting analysis of the present invention is to be used.

Assuming that the interacting analysis is used, the conditions which the object is expected to be exposed to during its lifetime are input in step 40. The particular conditions of concern are the stress applied to and temperature of the object, which may vary over time. In particular, a turbine rotor used is typically exposed to cycles of varying temperature and stress as the turbine is started, stopped and operated at different levels. The temperatures and stresses to which turbine rotors are exposed during a cycle are well known and the cycles which a turbine are likely to undergo can be predicted. Thus, this information can be input in step 40.

Different materials have different responses to temperature and stress which need to be taken into account in calculating remaining life, allowable stress, and initial allowable defect size. In programming a computer to use a method according to the present invention, there are several ways to allow for the variations in temperature, stress and material properties in performing the calculations. In the method illustrated in FIGS. 1A–1F, a file 42 is maintained with relationships between temperature and different materials that are to be analyzed by the program. The values corresponding to the material composing the selected turbine rotor and the cycles and temperatures input at step 40 are read in step 44. If the present invention is used to analyze objects which have little variation in composition, the values read in step 44 could be coded into the program used to analyze the indication.

Figure 1A:
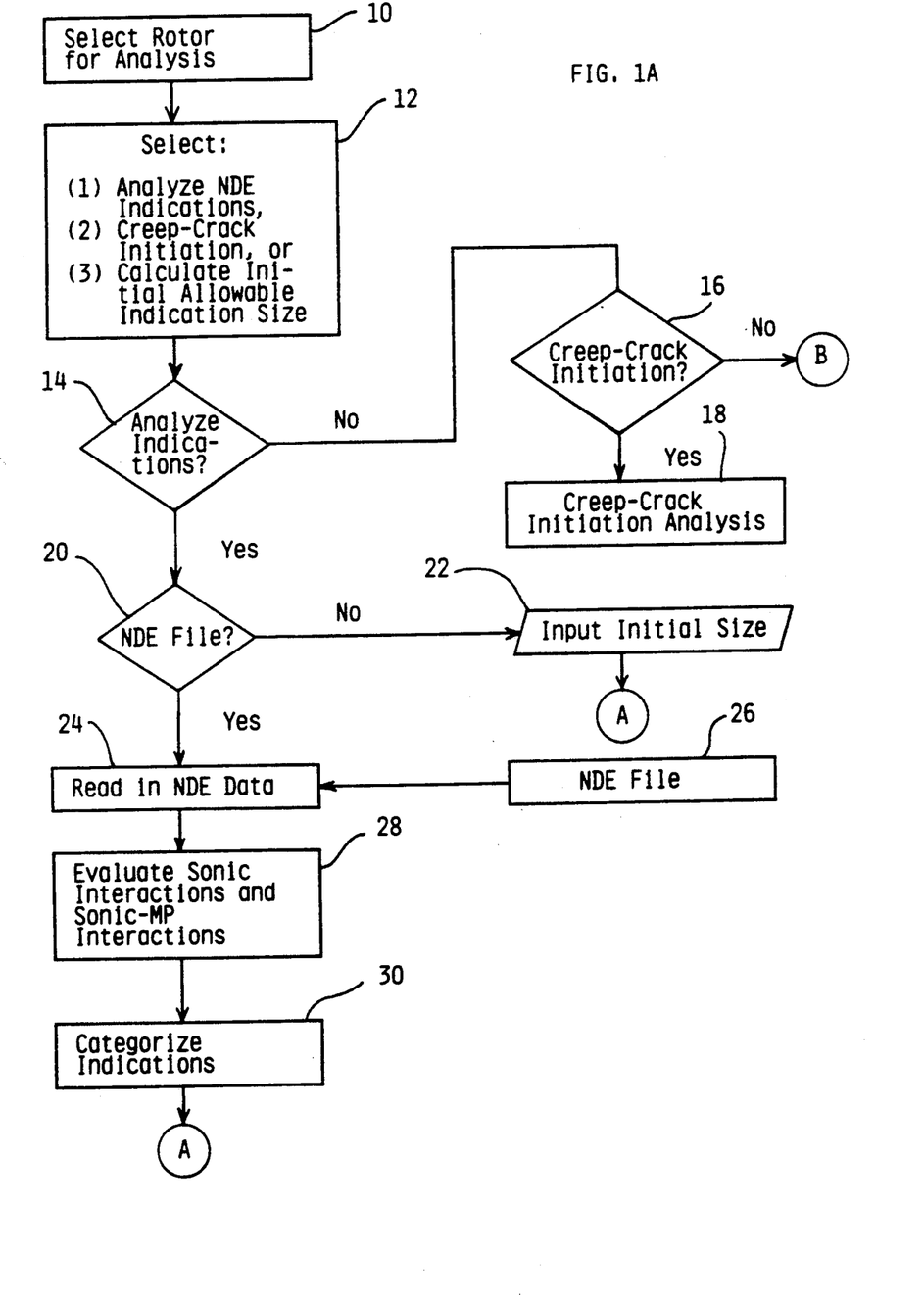
FIGS. 1A-1F are a flowchart of a method according to the present invention.

As indicated at 46, the following calculations are made to determine allowable stress for each of the indications. First, an estimate of the stress applied to the object at the location of the current indication is made in step 47. Next, in step 48 a stress intensity factor (K) is calculated for an indication based on a model defined by the category identified in step 30 (FIG. 1A). Methods of calculating K for various geometries are known in the art of fracture mechanics. For example, for a semi-elliptical crack, equation (1) can be used to calculate K:

$$K = 1.12\,\sigma\sqrt{\frac{\pi a}{Q}} \qquad (1)$$

where a=crack width, $\sigma$=stress and Q=a flaw shape parameter with a value of 1.22 for a width to length ratio of 0.2 and a value of 2.32 for a width to length ratio of 0.5. Other values of Q are known for differently shaped semi-elliptical cracks.

A critical crack size is then calculated in step 50 using "worst case" conditions 51 expected for the object and the material properties 42. During cold start conditions, the critical crack size $a_{cr}$ can be calculated according to equation (2).

$$a_{cr} = \left(\frac{K_{IC}}{1.12\,\sigma}\right)^2 \frac{Q}{\pi} \qquad (2)$$

where $K_{IC}$ is the critical value of K, called the fracture toughness of the material. It is a material constant determined from testing and is geometry independent. The parameter $\sigma$ is the cold start stress and Q is the flaw shape parameter used above.

In step 52, an appropriate crack growth law is selected for the conditions input in step 40. A current crack size (a) is set to the initial indication size of the indication (whether supplied from the NDE file 26 or input in step 22) as indicated in step 54. Next, the growth law selected in step 52 is applied to the current crack size in step 56 as the stress and temperature change according to the cycles and temperatures in step 40 until the current crack size is at least as large as the critical crack size calculated in step 50. The number of cycles accumulated in step 56 are compared with the specified number of cycles, or in other words the amount of time represented by the cycles is compared with the desired lifetime of the object in step 58. If the number of cycles is substantially different than the specified number, the stress assumed in step 47 is changed in step 60 and steps 50, 52, 54 and 56 are repeated starting with the calculation of a new critical crack size in step 50. If the number of cycles is substantially equivalent to the specified number, the allowable stress is output in step 62 and processing continues with the next indication in step 46 until all of the indications have been analyzed and processing stops in step 64. Of course, if only a single indication size is input in step 22, processing ends with the printing of allowable stress for that indication size and desired lifetime of the object.

Figure 1B:
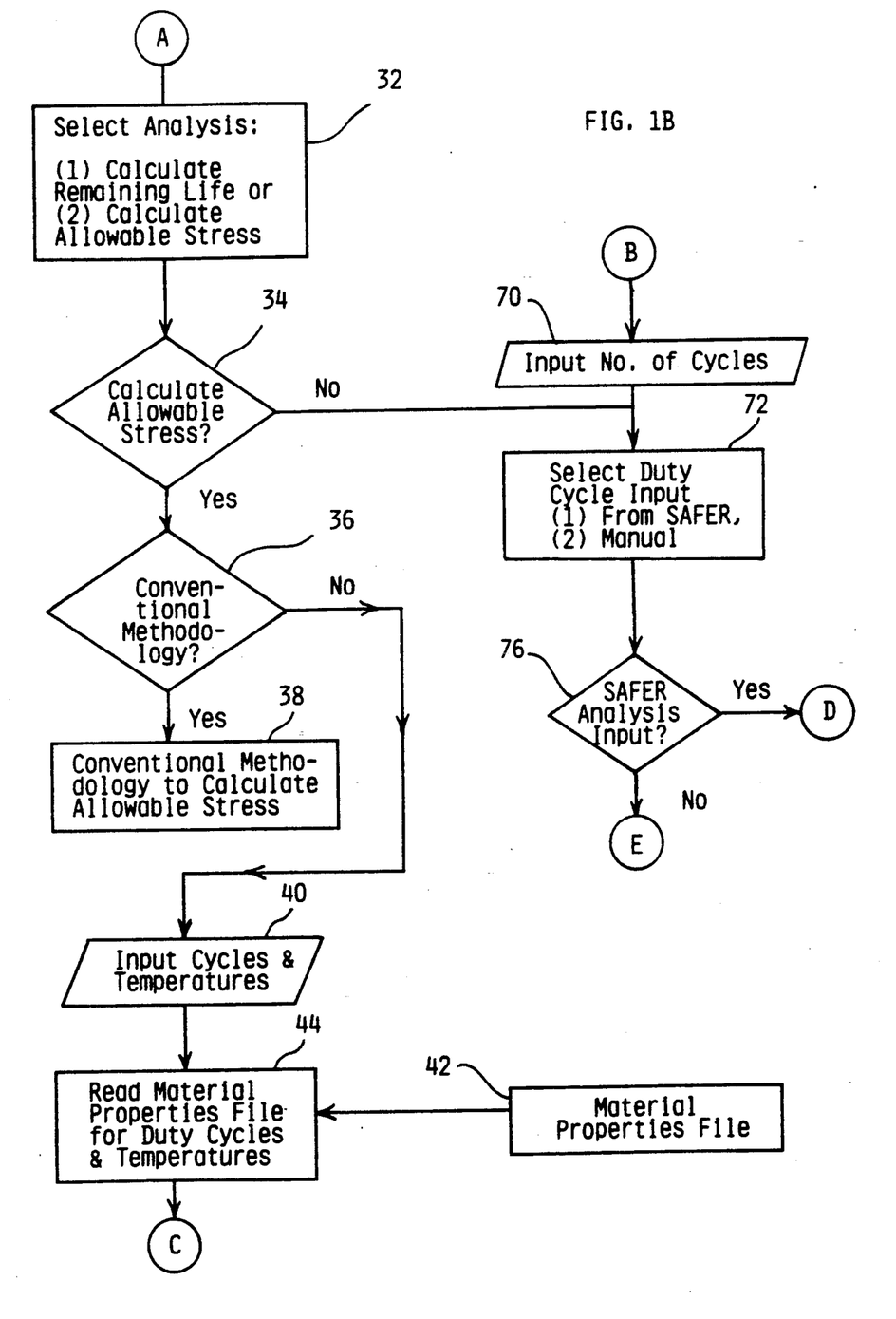
Figure 1C:
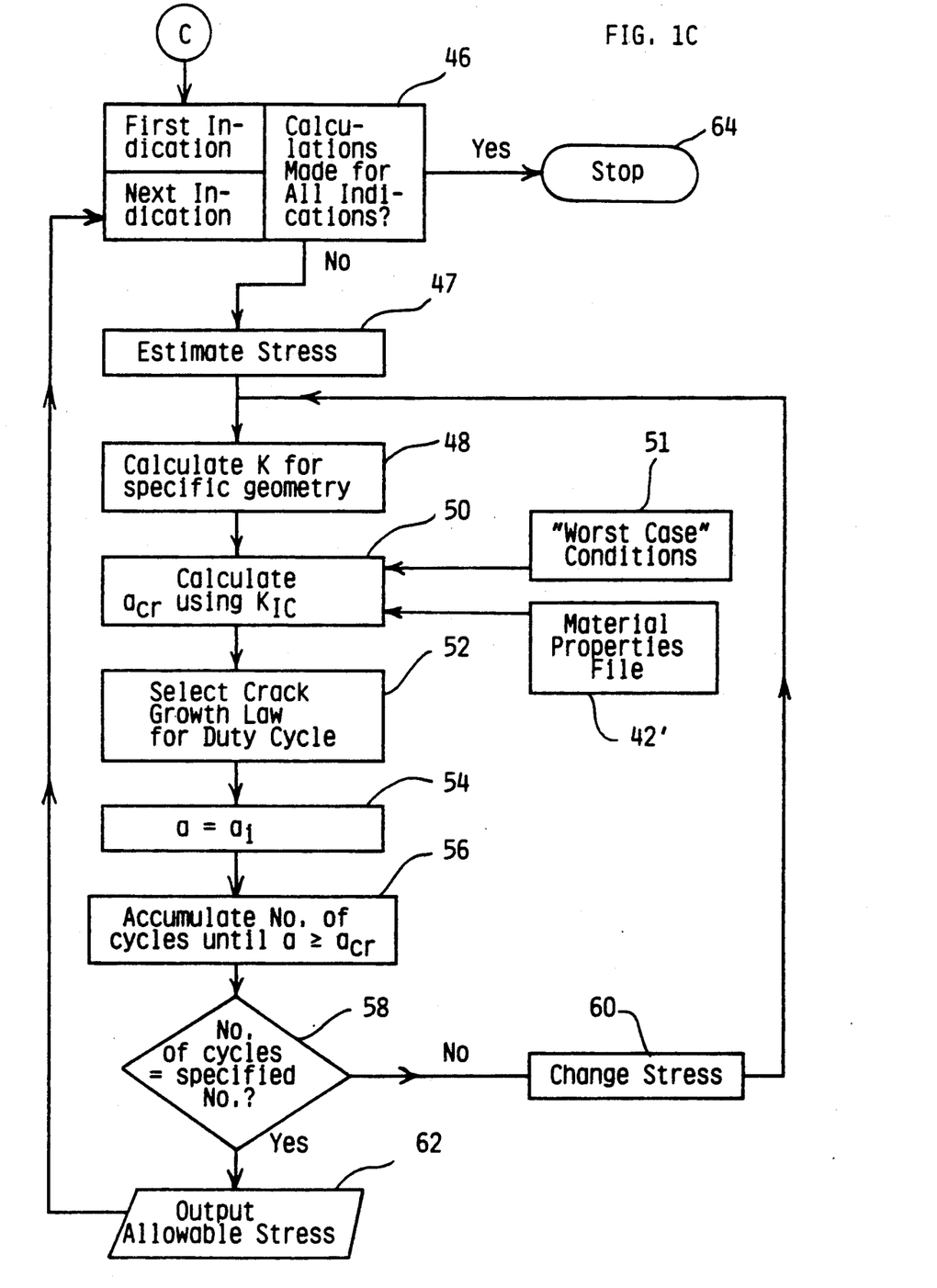
Figure 1D:
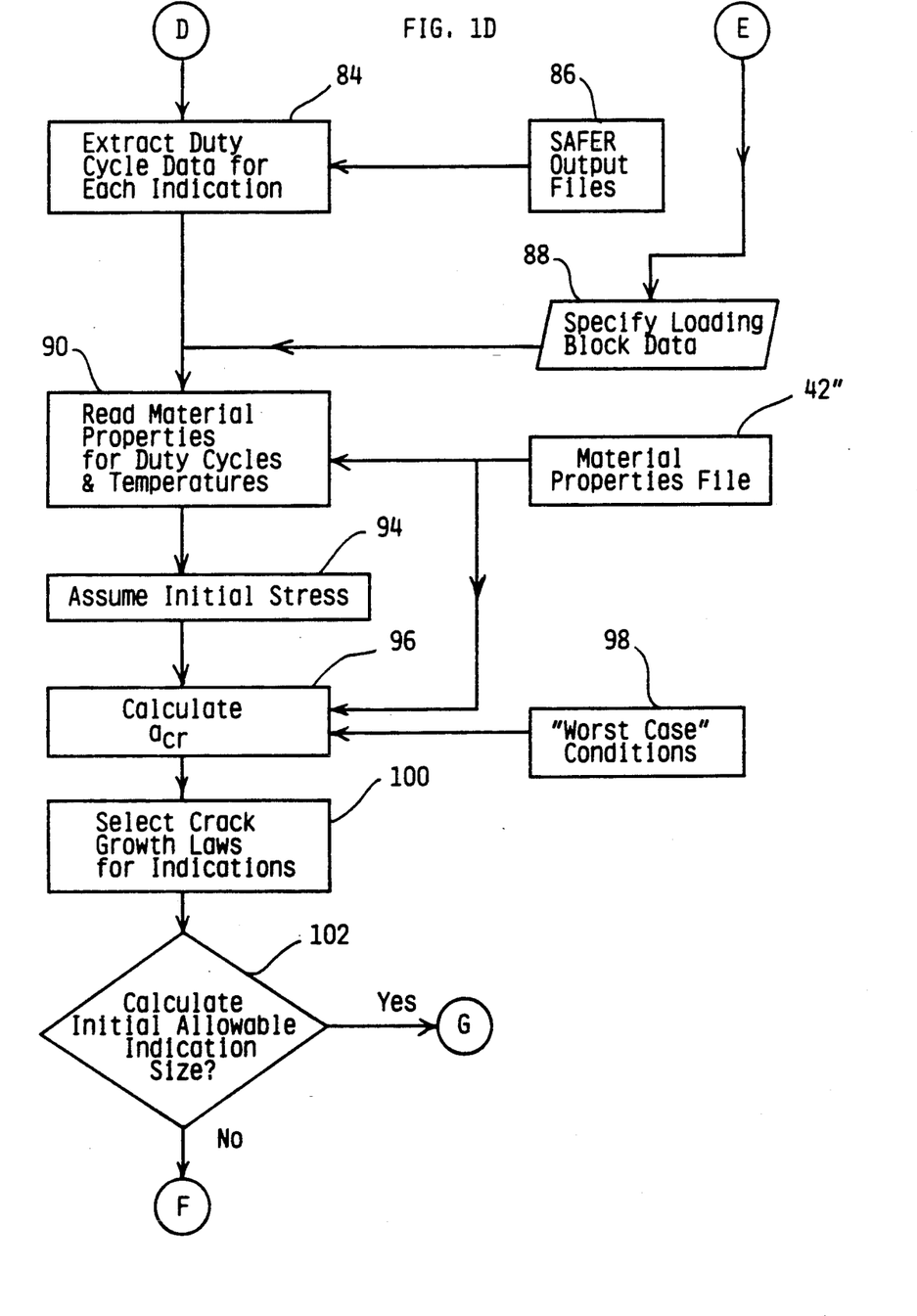
Figure 1E:
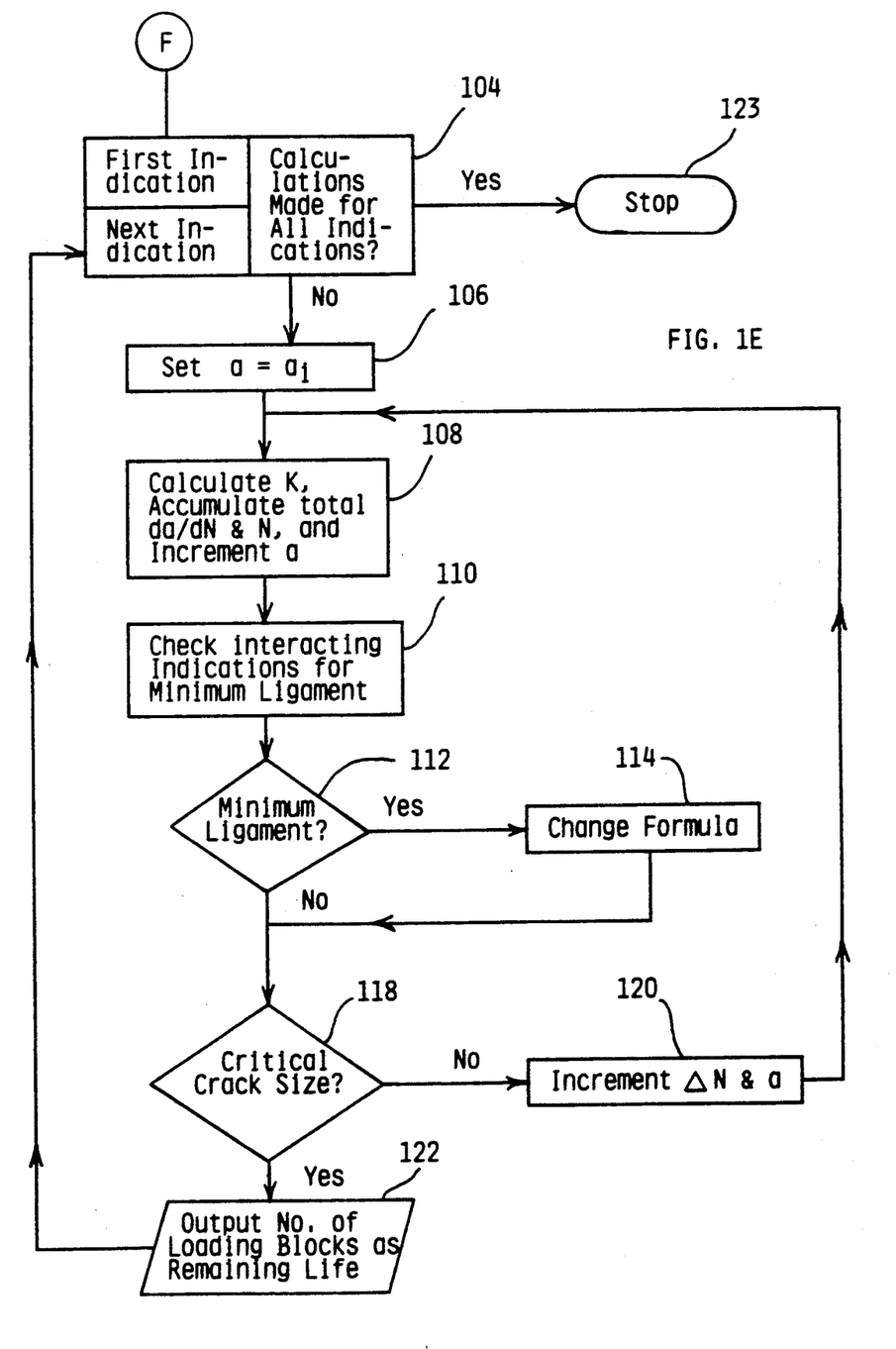

Returning to FIG. 1A, when the calculation of initial allowable indication size is selected in step 12, the decisions in step 14 and 16 result in step 70 in FIG. 1B to be executed next. In calculating an initial allowable indication size, no NDE data is used. However, it is necessary in step 70 to input the number of cycles which correspond to the desired lifetime of the rotor or other object.

The next step 72 is to select a duty cycle input method. The selection step 72 is used for inputting data to be used in calculation of an initial allowable indication size and, as indicated by line 74, also for calculation of the remaining life of the object. In the case of turbine rotors, an industry standard analysis package from Electric Power Research Institute (EPRI) is used for analyzing the distribution of temperature and stress in turbine rotors. This analysis package is called Stress and Fracture Evaluation of Rotors (SAFER) and provides detailed stress and temperature information which can be used as input to analyze a rotor according to the present invention. Alternatively, the desired information with a desired amount of detail can be input manually by any known method.

After the method of input is selected in step 72, it is determined in step 76 whether SAFER analysis will be used or the data will be input manually. Continuing with the processing illustrated in FIG. 1D, if SAFER analysis is used for input, step 84 extracts duty cycle data from SAFER output files 86 for each indication based upon the location of the indications. If manual input was selected in step 74, loading block data is input in step 88.

Regardless of how the cycle data is input, the material properties for the specified duty cycles and temperatures are input in step 90 from the material properties file 42". The material properties file 42" is physically the same as file 42 and 42' and step 90 is illustrated in FIG. 1B and described above for the calculation of allowable stress. The alternative methods for providing the information stored in the material properties file 42 described above with respect to step 44 also applies in the calculation of remaining life and initial allowable indication size.

Next, an initial stress is assumed in step 94 so that critical crack size $a_{cr}$ can be calculated in step 96 based upon "worst case" conditions 98 using equation (2) as described above for step 50. Next, the appropriate crack growth laws for the indications are selected in step 100 as described above for step 52. The preceding steps 90 through 100 are essentially the same in calculating both initial allowable indication size and remaining life. At step 102, the program determines whether calculation of initial allowable indication size was selected in step 12 or the calculation of remaining life was selected in step 32. If the calculation of remaining life was selected, processing continues with the steps illustrated in FIG. 1E.

As indicated in step 104, calculations are made for all of the indications. In step 106, the current crack size is assigned an initial value corresponding to one of the indications input in step 24 from the NDE file 26. Next in step 108, the stress intensity factor K is calculated for the particular geometry, the rate of fatigue crack growth (da/dN) and number of cycles (N) are accumulated and the current crack size (a) is incremented by the amount of growth indicated by the rate of growth and the increment in the number of cycles. The general formula for rate of fatigue crack growth is indicated in equation (3).

$$\frac{da}{dN} = C_1 \Delta K^{e1} + \left[ \frac{C_2}{K_h^{e2}} + \{C_3(t_r^{e3} - C_4)\Delta K^{e4} + C_5 t_h^{e5} K_h^{e6}\}^{-1} \right]^{-1} \quad (3)$$

where $\Delta K$ is the change in stress intensity factor, $K_h$ is the stress intensity factor during hold time, $t_r$ is the rise time and $t_h$ is the hold time at a particular temperature. The parameter values, i.e., the coefficients $C_1$ to $C_5$, and exponents e1 to e6, depend upon the material properties including temperature. The influence of the rise time of $t_r$ is often small and can be neglected to simplify equation (3). Also, in the case of conventional electrical power generating turbine rotors operated at a peak of 425° C. (800° F.) without any hold time and a cycle time of one second to ten minutes, the equation can be simplified with parameter values supplied as indicated in equation (4).

$$da/dN = 2.3 \times 10^{-9} (\Delta K)^{2.7} \quad (4)$$

If temperatures do not exceed 800° F., but there is a significant hold time, equation (3) can be simplified as indicated in equation (5).

$$\frac{da}{dN} = 7.2 \times 10^{-10} (\Delta K)^{2.7} + 3.0 \times 10^{-14} K_h^{5.6} \sqrt{t_h} \quad (5)$$

Finally, as an example of the parameter values supplied for equation (3) in the case of a conventional turbine rotor at 1000° F., the fatigue crack growth behavior is given by equation (6).

$$\frac{da}{dN} = 4.54 \times 10^{-9} (\Delta K)^{2.51} + \left[ \frac{1.2 \times 10^{13}}{(K_h)^{7.3}} + \{9.55 \times 10^{-7} (t_r^{0.263} - 0.069)(\Delta K)^{1.454} + 1.06 \times 10^{-6} (t_h)^{0.365} (K_h)^{1.27}\}^{-1} \right]^{-1} \quad (6)$$

Equations (3)-(6) are similar to those available in the literature on the analysis of crack growth behavior in turbine rotors. Similar equations for turbine rotors or other materials at other temperatures and cycles can be obtained from the literature or by following the procedures which were used to obtain the above equations as described in the literature on crack growth behavior.

In step 110, all indications are checked for minimum ligament distance in step 110. If a minimum ligament distance, based on the plastic zone size at the crack tip, is found in step 112, the formula is changed in step 114. Next, if the current crack size (a) is still less than the critical crack size ($a_{cr}$), the next cycle increment is selected in step 120 and steps 108, 110 and 112 are repeated. If the current crack size is greater than or equal to the critical crack size, the number of loading blocks is output as the remaining life in step 122 and processing continues with the next indication in step 104 until calculations have been made for all indications and processing stops in step 123.

Figure 1F:
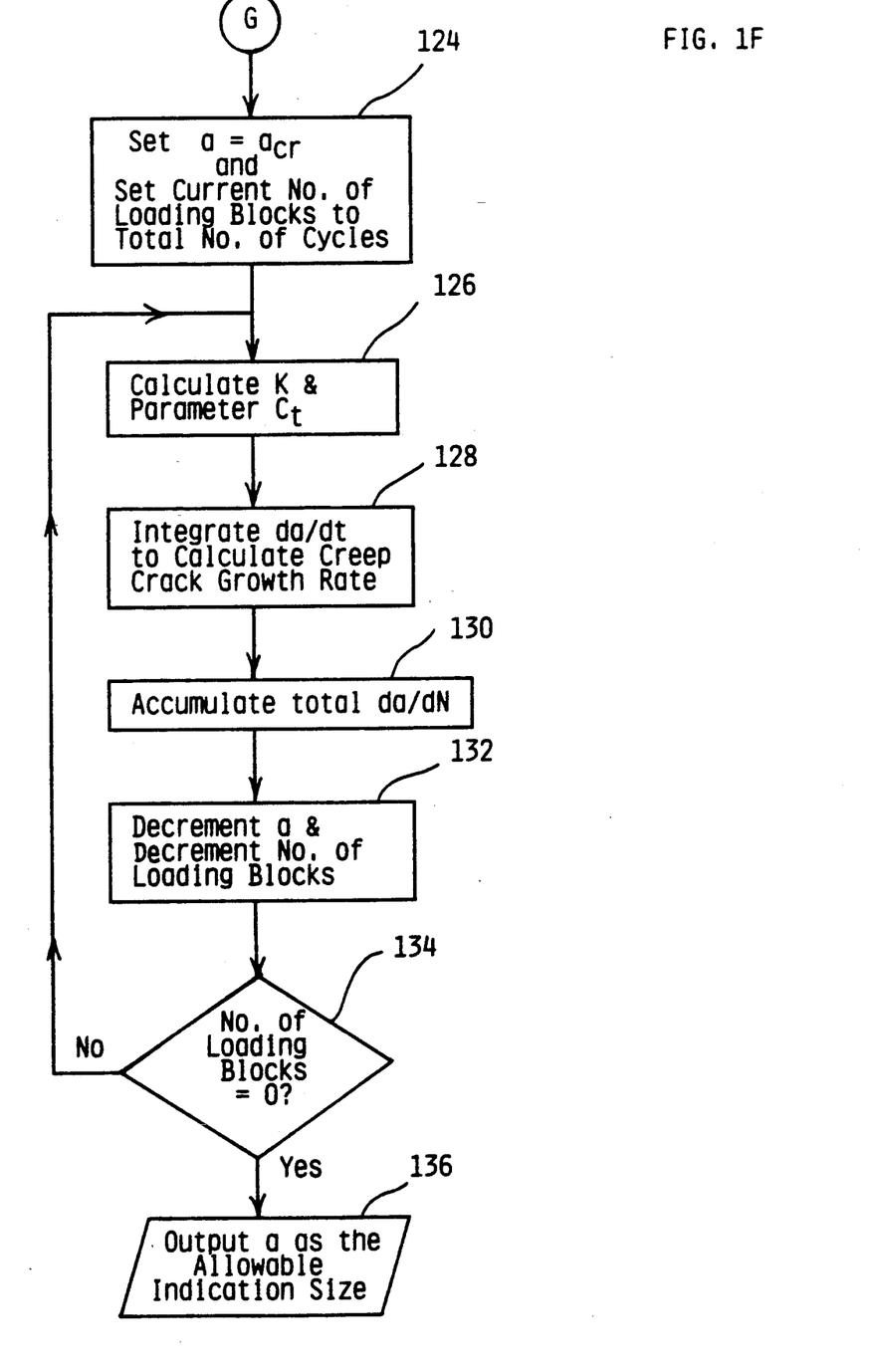

If it is determined in step 102 (FIG. 1D) that the calculation of initial allowable indication size was selected in step 12, processing continues with step 124 illustrated in FIG. 1F. The calculation of an initial allowable indication size begins with assigning the critical crack size ($a_{cr}$) calculated in step 96 to a current crack size (a) and setting a current number of loading blocks equal to the number of loading blocks specified by the number of cycles input in step 70. Next, the stress intensity factor (K) is calculated as described above with respect to steps 48 and 116. In addition, parameter(s), such as Ct, are also calculated in step 126 based upon the indication geometry, material properties and temperature and stress to which the object will be exposed. The values of K and the parameter(s) calculated in step 126 are used in steps 128 and 130 to integrate da/dt to calculate the creep crack growth rate and then to accumulate the rate of fatigue crack growth (da/dN) as described above with respect to step 108. Creep crack growth rate as a function of hold time can be calculated from equation (7).

$$\frac{da}{dt} = BC_t^q \quad (7)$$

For example, a turbine rotor held at a temperature of 1000° F. for less than 24 hours has a creep crack growth rate defined by equation (8).

$$\frac{da}{dt} = 1.39 \times 10^{-4} C_t^{0.62} \quad (8)$$

In step 132, the current crack size (a) is decremented by the amount of creep crack growth and fatigue crack growth calculated in steps 128 and 130 for a cycle portion which is subtracted from the current number of loading blocks set in step 124.

As indicated in step 134, steps 126, 128, 130 and 132 are repeated until the current number of loading blocks is approximately equal to zero. By this time, the current crack size (a) has been reduced to a value which represents the allowable indication size. Thus, the current crack size (a) can be output in step 136 as the allowable indication size. This information can then be compared to the indication sizes obtained from NDE tests of an object to determine suitability of the object to use in the environment represented by the loading blocks used in the analysis described with respect to FIG. 1F.

While the terms "object" and "turbine rotor" have been used for most part interchangeably in the above description of the preferred embodiment, the present invention is not limited to analysis of turbine rotors. Many types of equipment are exposed to cyclical stress changes or stress at temperatures where creep crack growth is significant. A method according to the present invention can be used to analyze crack growth under both types of conditions. In addition, many types of objects have minute discontinuities in their structure which can become cracks as the object is subjected to stress over a long period of time. The growth of these cracks and interaction of the cracks with one another can be analyzed using the present invention, based upon estimates of the stress, temperature and other factors to which the object is exposed.

The many features and advantages of the present invention are apparent from the detailed specification and thus, it is intended by the appended claims to cover all such features and advantages of the method which fall within the true spirit and scope of the invention. Further, since numerous modifications and changes will readily occur to those skilled in the art, it is not desired to limit the invention to the exact construction and operation illustrated and described. Accordingly, all suitable modifications and equivalents may be resorted to falling within the scope and spirit of the invention.

What is claimed is:

1. A method of evaluating effects of stress and temperature on an object after analysis to detect indications of discontinuities in the object, where at least part of the stress is applied to the object at a temperature where creep is a significant factor for the material composing the object, comprising the steps of:
    (a) identifying indications likely to interact by using a computer program to apply predetermined criteria to the indications;
    (b) categorizing by interaction type each of the indications identified in step (a); and
    (c) applying different computer models of crack growth to the indications in dependence upon the interaction type determined by said identifying in step (a) and said categorizing in step (b) to determine a relationship between indication size, stress applied to the object and remaining life of the object, said applying comprising the steps of:
        (ci) defining the stress applied to and temperature of the object as a function of time;
        (cii) calculating a stress intensity factor for each of the indications;
        (ciii) accumulating change in the indication size of each of the indications over a period of time;
        (civ) combining interacting indications within a minimum ligament distance to produce a new indication; and
        (cv) repeating steps (cii) through (civ) until the indication size of one of the indications is at least as large as a critical crack size.

2. A method as recited in claim 1, further comprising the step of (d) outputting the remaining life of the object in dependence upon an amount of time represented by said accumulating in step (ciii) when the indication size of the one of the indications reaches the critical crack size in step (cv).

3. A method of evaluating effects of stress and temperature on an object after analysis to detect indications of discontinuities in the object, where at least part of the stress is applied to the object at a temperature where creep is a significant factor for the material composing the object, comprising the steps of:
    (a) identifying indications likely to interact by using a computer program to apply predetermined criteria to the indications;
    (b) categorizing by interaction type each of the indication identified in step (a); and
    (c) applying different computer models of crack growth to the indications in dependence upon the interaction type determined by said identifying in step (a) and said categorizing in step (b) to determine a relationship between indication size, stress applied to the object and remaining life of the object, said applying comprising the steps of:
        (ci) combining interacting indications within a minimum ligament distance to produce a new indication; and
        (cii) applying one of the models of crack growth to the new indication produced by combining the interacting indications in step (ci).

4. A method of evaluating effects of stress and temperature on an object after analysis to detect indications of discontinuities in the object, comprising the steps of:
    (a) identifying indications likely to interact by using a computer program to apply predetermined criteria to the indications;
    (b) categorizing by interaction type each of the indications identified in step (a); and
    (c) applying different computer models of crack growth to the indications in dependence upon the interaction type determined by said identifying in step (a) and said categorizing in step (b) to determine a relationship between indication size, stress applied to the object and remaining life of the object, said applying comprising the steps of:
        (ci) calculating a stress intensity factor for one of the indications;
        (cii) initializing crack size to a size represented by the one of the indications;
        (ciii) accumulating crack growth as a function of time at an assumed stress level by applying one of the models of crack growth selected for one of the indications until the crack size is at least as large as a critical crack size;

(civ) comparing an amount of time represented by the crack growth in step (ciii) with a desired lifetime for the object;

(cv) repeating steps (cii) through (civ) after changing the assumed stress level if said comparing in step (civ) found the amount of time and the desired lifetime of the object to be substantially different; and (cvi) outputting for each of the indications the assumed stress level as an allowable stress for the object if said comparing in step (civ) found the amount of time and desired lifetime of the object to be substantially equivalent.

5. A method as recited in claim 4,
wherein steps (ci) through (cv) are repeated for each of the indications, and
wherein step (ciii) comprises combining indications within a minimum ligament distance to produce a new indication.

6. A method as recited in claim 5, wherein the stress varies cyclically over time, and
wherein step (ciii) comprises accumulating cycles of stress changes defined in loading blocks.

7. A method of evaluating effects of stress on an object, at least part of the stress being applied at a temperature where creep is a significant factor for the material composing the object, comprising the steps of:

(a) establishing a relationship between time and stress applied to and temperature of the object;

(b) calculating a critical crack size for worst case conditions;

(c) assigning an initial value to a current crack size;

(d) calculating a stress intensity factor and a crack growth rate for the current crack size in dependence upon the relationship between time and stress established in step (a) and including effects of creep;

(e) changing the current crack size in dependence upon the said calculating of crack growth rate in step (d); and (f) repeating steps (d) and (e) in a computing apparatus until one of remaining life of the object and an initial allowable discontinuity indication size is determined.

8. A method as recited in claim 7, wherein the stress varies cyclically over time, and
wherein step (d) comprises accumulating cycles of stress changes defined in loading blocks.

9. A method as recited in claim 8,
further comprising the step of (g) accumulating the crack growth rate,
wherein step (c) comprises assigning one of an existing and an estimated indication size to the current crack size,
wherein step (e) comprises incrementing the current crack size after said accumulating in steps (d) and (g), and
wherein step (f) comprises repeating steps (d), (e), and (g) until the current crack size is substantially equivalent to the critical crack size calculated in step (b) to determine the remaining life of the object as a number of loading blocks accumulated in step (d).

10. A method as recited in claim 8,
wherein step (c) comprises assigning the critical crack size to the current crack size,
wherein step (e) comprises decrementing the current crack size,
wherein step (f) comprises repeating steps (d) and (e) a number of times corresponding to a period of time substantially equivalent to a desired lifetime of the object, and
wherein said method further comprises the step of (g) outputting the current crack size as an initial allowable indication size.

11. A method for evaluating effects of stress on a turbine rotor exposed to cyclical changes in stress and temperature, comprising the steps of:

(a) obtaining an estimate of at least one indication of discontinuity in material composing the turbine rotor;

(b) recording in machine readable form a number of loading blocks defining cycles of temperature and stress upon the turbine rotor; and (c) applying different models of crack growth to the indication of discontinuity, including interactions between indications when estimates for more than one indication are obtained in step (a), and including effects of creep when the loading blocks recorded in step (b) include exposure of the turbine rotor to a temperature where creep is a significant factor in crack growth in the material composing the turbine rotor.

12. A method as recited in claim 11, further comprising the steps of:

(d) identifying interacting indications among the indications by using a computer program to apply predetermined criteria to the indications;

(e) categorizing by interaction type each of the indications identified in step (d); and (f) repeating step (c) until one of allowable stress and remaining life of the rotor is determined.

13. A method as recited in claim 12,
further comprising the step of (g) combining pairs of the interacting indications within a minimum ligament distance to produce a new indication,
wherein step (f) comprises repeated iterations of steps (c), (d), and (e), and
wherein step (c) comprises applying the models of crack growth to the indications defined for each of the iterations in dependence upon size and location of the indications, including each new indication produced in step (g).

14. A method as recited in claim 13,
wherein step (c) further comprises the steps of:
(ci) calculating a stress intensity factor for each of the indications; and
(cii) accumulating change in the indication size of each of the indications in dependence upon change in the loading blocks,
wherein step (f) comprises repeating steps (c), (d) and (e) until the indication size of one of the indications is at least as large as a critical crack size, and
wherein said method further comprises the step of (h) outputting the remaining life of the object in dependence upon an amount of time represented by the number of loading blocks included in said accumulating in step (cii) when the indication size of the one of the indications reaches the critical crack size in step (f).

15. A method as recited in claim 13, (ci) calculating a stress intensity factor for one of the indications;

(cii) initializing crack size to a size represented by the one of the indications;

(ciii) accumulating crack growth as a function of time at an assumed stress level by applying one of the models of crack growth selected for the one of the indications until the crack size is at least as large as a critical crack size;

(civ) comparing an amount of time represented by the crack growth in step (ciii) with a desired lifetime for the object;

(cv) repeating steps (cii) through (civ) after changing the assumed stress level if said comparing in step (civ) found the amount of time and the desired lifetime of the object to be substantially different; and (cvi) outputting the assumed stress level as an allowable stress for the object if said comparing in step (civ) found the amount of time and desired lifetime of the object to be substantially equivalent.

16. A method as recited in claim 11, wherein step (a) comprises assigning a critical crack size to a current crack size as the estimate of one indication of discontinuity, and wherein said method further comprises the steps of:

(d) setting a current number of loading blocks equal to all the loading blocks recorded in step (b);

(e) calculating a stress intensity factor and a crack growth rate parameter for the current crack size;

(f) accumulating creep crack growth and fatigue crack growth;

(g) decrementing the current crack size and the current number of loading blocks;

(h) repeating steps (e), (f) and (g) if the current number of loading blocks is substantially greater than zero; and (i) outputting the current crack size as an allowable indication size if the current number of loading blocks is substantially equal to zero.

* * * * *